United States Patent [19]
Simon

[11] Patent Number: 5,401,728
[45] Date of Patent: Mar. 28, 1995

[54] LECITHIN BASED TOPICAL LINIMENT

[76] Inventor: John A. Simon, 16215 White Star Dr., Houston, Tex. 77062

[21] Appl. No.: 73,891

[22] Filed: Jun. 9, 1993

Related U.S. Application Data

[63] Continuation-in-part of Ser. No. 861,943, Apr. 2, 1992, abandoned.

[51] Int. Cl.⁶ ............ A61K 35/78; A61K 33/06; A61K 31/685; A61K 31/14
[52] U.S. Cl. .................. 514/78; 424/195.1; 424/682; 514/557; 514/642; 514/817; 514/825; 514/855; 514/937; 554/80; 562/8; 564/293
[58] Field of Search ............ 514/78, 557, 642; 424/682, 195.1; 554/80; 562/8; 564/293

[56] References Cited

U.S. PATENT DOCUMENTS

| | | | |
|---|---|---|---|
| 4,427,670 | 6/1984 | Ofuchi et al. | 424/241 |
| 4,665,069 | 5/1987 | Rosenberg | 514/222 |
| 4,719,239 | 1/1988 | Muller et al. | 514/785 |
| 4,952,560 | 8/1990 | Kigasawa et al. | 514/2 |
| 5,043,323 | 8/1991 | Bombardelli et al. | 514/25 |
| 5,153,000 | 10/1992 | Chikawa et al. | 424/450 |

*Primary Examiner*—John W. Rollins
*Assistant Examiner*—Howard C. Lee
*Attorney, Agent, or Firm*—Kenneth A. Roddy

[57] ABSTRACT

A soybean lecithin based topical liniment and method of making the same is disclosed. The liniment utilizes soybean lecithin as a base and major ingredient and as the emulsifier which is mixed with plant oils, natural menthol, calcium stearate, and magnesium stearate. The soybean lecithin, plant oils, natural menthol, calcium stearate, and magnesium stearate are mixed together in predetermined relative proportions with the amount of soybean lecithin being greater than the sum of the amounts of the plant oils, natural menthol, calcium stearate, and magnesium stearate. The soybean lecithin, plant oils, natural menthol, calcium stearate, and magnesium stearate are added to one another and mixed together in a predetermined sequence to prevent precipitation and provide a homogenous mixture having a viscosity suitable for topical application.

3 Claims, No Drawings

LECITHIN BASED TOPICAL LINIMENT

CROSS REFERENCE TO RELATED APPLICATION

This application is a continuation-in-part of U.S. patent application Ser. No. 07/861,943, filed Apr. 2, 1992, now abandoned.

BACKGROUND OF THE INVENTION

1. Field of the Invention

This invention relates generally to topical liniments, and more particularly to a soybean lecithin based topical liniment utilizing a mixture of soybean lecithin as a base and emulsifier, plant oils, natural menthol, calcium stearate, and magnesium stearate.

2. Brief Description of the Invention

There are many "over the counter" (OTC) drugs which claim to provide relief from a variety of human conditions, such as muscle aches, cramps, arthritis, muscle spasms, nasal congestion, and headache. Some of the common "over the counter" drugs are; Ben Gay (TM Pfeizer, Inc.), Sportscream (TM Thompson Medical Co., Inc.), Therapeutic Mineral Ice (TM Bristol-Myers Co.), Sero-Ice (TM Seroyal Brands, Inc.), Eucalyptamint (TM Naturapathic Laboratories, Inc.), Flex-al (TM Chatten, Inc.), and Vicks Inhaler (TM Proctor & Gamble Co.).

Ben Gay (TM Pfeizer, Inc.) has 15% methyl salicytate and 10% menthol listed as active ingredients. Listed as inactive inactive ingredients are glycerol stearate, lanolin, prolysorbate-85, purified water, sorbitan tristearate, stearic acid, and triethanolamine.

Sportscream (TM Thompson Medical Co., Inc.) has 10% salycin as its active ingredient with "other ingredients" listed as; cetyl alcohol, FD&C Blue No. 1, FD&C Yellow No. 5, fragrance, glycerin, methylparaben, mineral oil, potassium phosphate monobasic, propylparaben, stearic acid, triethanolamine, and water.

Therapeutic Mineral Ice (TM Bristol-Myers Co.) has menthol listed as the active ingredient. Unlike Sportscream, Ben Gay, and other "over the counter" drugs, the percent of menthol is not displayed on the label. The cool, blue, Thereapeutic Mineral Ice gel base is specifically formulated to dry quickly with no grease or lingering unpleasant odor. Thereapeutic Mineral Ice is one of the most widely advertised over the counter drugs.

Sero-Ice (TM Seroyal Brands, Inc.) has 6.25% menthol as its active ingredient. Inactive ingredients listed are; N-propyl alcohol, eucalyptus oil, origanum oil, tincture of merthiolate, and deionized water.

Eucalyptamint (TM Naturapathic Laboratories, Inc.) is one of the latest widely advertised pain relieving over the counter drugs on the market. Its active ingredient is 15% natural menthol. Other ingredients are lanolin and eucalyptus oil.

Flex-al (TM Chatten, Inc.) was also introduced in the market quite recently. Its label states; "Active ingredient: menthol (7%) in Flex-al 454's special Aloe Vera Gel also containing alcohol, allantoin, aloe vera gel, boric acid, carbomer 940, diazolidinyl urea, eucalyptus oil, glycerin, iodine, methylparaben, methyl salicylate, peppermint oil, polysorbate 60, potassium iodide, propylene gycol, propyl paraben, thyme oil, triethanolamine, water, 97–116."

Vicks Inhaler (TM Proctor & Gamble Co.) has been on the market for many years. Its active ingredient is 1-desoxyephedrine. Inctive ingredients listed are; special Vicks Vapors (bornyl acetate), camphor, lavender oil, and menthol.

Typically, over the counter drugs contain active ingredients which consist of one or more counterirritants, anti-inflammatory agents and/or antispasmodic agents. Listed generally under "other ingredients" or "inactive ingredients" are; alcohols, animal byproducts, petroleum byproducts, saturated organic acids, salicylates or their derivatives, and many synthetic chemicals.

The present invention is distinguished over the prior art in general, and these over the counter drugs in particular by a lecithin based topical liniment which utilizes soybean lecithin as a base and major ingredient and as the emulsifier, and does not incorporate aspirin or petroleum byproducts. The soybean lecithin is mixed with plant oils, natural menthol, calcium stearate, and magnesium stearate. The soybean lecithin, plant oils, natural menthol, calcium stearate, and magnesium stearate are mixed together in predetermined relative proportions with the amount of soybean lecithin being greater than the sum of the amounts of the plant oils, natural menthol, calcium stearate, and magnesium stearate. The soybean lecithin, plant oils, natural menthol, calcium stearate, and magnesium stearate are added to one another and mixed together in a predetermined sequence to prevent precipitation and provide a homogenous mixture having a viscosity suitable for topical application.

SUMMARY OF THE INVENTION

It is therefore an object of the present invention to provide a lecithin based topical liniment which can be used for the relief of nasal congestion.

It is another object of this invention to provide a lecithin based topical liniment which can be used for the relief of headaches.

Another object of this invention is to provide a lecithin based topical liniment which can be used for the relief of muscle aches and arthritic pain.

A further object of this invention is to provide a lecithin based topical liniment which utilizes soybean lecithin as a base and major ingredient and as the emulsifier for the mixture.

A still further object of this invention is to provide a lecithin based topical liniment which contains a mixture of soybean lecithin, plant oils, natural menthol, calcium stearate, and magnesium stearate.

Other objects of the invention will become apparent from time to time throughout the specification and claims as hereinafter related.

The above noted objects and other objects of the invention are accomplished a lecithin based topical liniment which utilizes soybean lecithin as a base and major ingredient and as the emulsifier. The soybean lecithin is mixed with plant oils, natural menthol, calcium stearate, and magnesium stearate. The soybean lecithin, plant oils, natural menthol, calcium stearate, and magnesium stearate are mixed together in predetermined relative proportions with the amount of soybean lecithin being greater than the sum of the amounts of the plant oils, natural menthol, calcium stearate, and magnesium stearate. The soybean lecithin, plant oils, natural menthol, calcium stearate, and magnesium stearate are added to one another and mixed together in a predetermined sequence to prevent precipitation and provide a homogenous mixture having a viscosity suitable for topical application.

DESCRIPTION OF THE PREFERRED EMBODIMENT

The present invention is a lecithin based topical liniment which utilizes soybean lecithin as a base and major ingredient and as the emulsifier. The soybean lecithin is mixed with plant oils, natural menthol, calcium stearate, and magnesium stearate. The soybean lecithin, plant oils, natural menthol, calcium stearate, and magnesium stearate are mixed together in predetermined relative proportions with the amount of soybean lecithin being greater than the sum of the amounts of the plant oils, natural menthol, calcium stearate, and magnesium stearate. The plant oils include: lemon grass oil, clove oil, eucalyptus oil, lemon oil, camphor oil, lime oil, and ginger oil.

The formulation is the outcome of numerous trials using various combinations of mixtures, and is based on the inventor's knowledge of Indian Ayurvec medicine and biochemistry. The combination of ingredients and the relative proportions of the ingredients to each other were established after extensive experimentation. The preferred lecithin based topical liniment is a mixture in parts per gallon of: approximately 8.5 cups of soybean lecithin as a base ingredient and emulsifier; approximately 1040 ml. of plant oils; approximately 560 g. of natural menthol; approximately 10 g. of calcium stearate; and approximately 5 g. of magnesium stearate.

The preferred proportions of the plant oils in parts per gallon are: approximately 345 ml. of lemon grass oil, approximately 230 ml. of clove oil, approximately 190 ml. of eucalyptus oil, approximately 125 ml. of lemon oil, approximately 100 ml. of camphor oil, approximately 40 ml. of lime oil, and approximately 10 ml. of ginger oil.

After several trials, it was discovered that the sequence of adding the ingredients would also affect the homogeneity and viscosity of the finished product. It was found that the following sequence of adding and mixing the ingredients produced the best results. (1) Adding the following ingredients in the sequence as listed; natural menthol, calcium stearate, magnesium stearate, lemon grass oil, clove oil, eucalyptus oil, lemon oil, camphor oil, and lime oil. (2) Mixing the ingredients by shaking intermittently for 3 minutes. (3) Adding the soybean lecithin and mixing the ingredients by rotating the container for 3 minutes and allowing the mixture to stand overnight. (4) After 24 hours, adding the ginger oil to the mixture and rotating the container for 3 minutes. On the third day, the mixture would be ready for bottling and use.

Soybean lecithin was selected as the base and major ingredient of the liniment for two reasons. First, soybean lecithin contains choline and acetylcholine. The choline is a precursor for the acetylcholine, and the acetylcholine is a neurotransmitter which plays a major role in the transmission of nerve impulses. Second, lecithin acts as an emulsifier for the plant oils, natural menthol, calcium stearate, and magnesium stearate.

Various other relative proportions of the soybean lecithin, plant oils, natural menthol, calcium stearate, and magnesium stearate may be used, with resultant variations in the homogeneity and viscosity. Calcium stearate and magnesium stearate, by themselves, are not readily miscible in some of the plant oils which are used in the mixture, and the ratio of calcium stearate to magnesium stearate will effect solubility. Various ratios of calcium stearate to magnesium stearate may be used, but will produce precipitation of these materials. An amount of calcium stearate greater than the amount of magnesium stearate will produce a satisfactory soluble stearate mixture. Providing the soybean lecithin in an amount greater than the sum of the amounts of the plant oils, natural menthol, calcium stearate, and magnesium stearate, will produce a desirable homogenous mixture having a viscosity suitable for topical application.

The sequence of adding and mixing the ingredients also affects the finished product. For example, if the soybean lecithin is mixed with the natural menthol, calcium stearate, magnesium stearate, lemon grass oil, clove oil, eucalyptus oil, lemon oil, camphor oil, lime oil, and ginger oil, at the same time, the resultant mixture will develop a less than desirable fragrance 24 hours after the initial mixing.

After experimentation, it was found that by deleting the ginger oil from the initial mixture, mixing the soybean lecithin with the natural menthol, calcium stearate, magnesium stearate, lemon grass oil, clove oil, eucalyptus oil, lemon oil, camphor oil, and lime oil, allowing the recited mixture to stand for at least 24 hours after the initial mixing, and then adding the ginger oil, that the resultant mixture would have a desirable pleasant fragrance.

Thus, various ratios of the ingredients may be used to produce a liniment with resultant variations in homogeneity, viscosity, and fragrance. However, the preferred mixture is one in which soybean lecithin is used as the base and emulsifier and is mixed with natural menthol, calcium stearate, magnesium stearate, lemon grass oil, clove oil, eucalyptus oil, lemon oil, camphor oil, and lime oil, in the amounts described previously, allowed to stand for at least 24 hours after the initial mixing, and then ginger oil in the amount described previously, is added to the mixture. In the preferred mixture, the ratio of calcium stearate to magnesium stearate is sufficient to prevent precipitation, and the ratio of the soybean lecithin relative to the other ingredients is an amount greater than the sum of the amounts of the plant oils, natural menthol, calcium stearate, magnesium stearate, and ginger oil. This combination of ingredients and the manner at sequence in which they are mixed will produce a desirable homogenous liniment mixture having a viscosity suitable for topical application, and a pleasant fragrance.

It should be noted that the recited ingredients are of plant origin, with the exception of calcium stearate and magnesium stearate. Among the eleven ingredients utilized in the described mixture, menthol and camphor are regulated by the Food And Drug Administration (FDA), and must conform to the monograph published in the Feb. 8, 1983 Federal Register. Therefore, the maximum allowable concentration of these ingredients must not exceed the published guidelines. The inventor is not aware of any FDA regulations regarding the other ingredients.

While this invention has been described fully and completely with special emphasis upon a preferred embodiment, it should be understood that within the scope of the appended claims the invention may be practiced otherwise than as specifically described herein.

I claim:

1. A homogeneous lecithin based topical liniment for aiding in the transmission of nerve impulses in the area of application comprising a mixture in parts per gallon of:

a. about 8.5 cups of soybean lecithin as a base ingredient and emulsifier, said soybean lecithin containing sufficient amounts of choline and acetylcholine such that said choline serves as a precursor for said acetylcholine and said acetylcholine serves as a neurotransmitter to aid in the transmission of nerve impulses;

b. plant oils consisting of about 345 ml. lemon grass oil, about 230 ml. clove oil, about 190 ml. eucalyptus oil, about 125 ml. lemon oil, about 100 ml. camphor oil, about 40 ml. lime oil, and about 10 ml. ginger oil;

c. about 560 g. of natural menthol;

d. about 10 g. of calcium stearate; and e. about 5 g. of magnesium stearate.

2. A homogeneous lecithin based topical liniment product for aiding in the transmission of nerve impulses in the area of application made by the process of:

mixing together in parts per gallon about 560 g. natural menthol, about 10 g. calcium stearate, about 5 g. magnesium stearate, about 345 ml. lemon grass oil, about 230 ml. clove oil, about 190 ml. eucalyptus oil, about 125 ml. lemon oil, about 100 ml. camphor oil, and about 40 ml. lime oil, in the sequence as listed;

adding about 8.5 cups soybean lecithin and mixing it with the recited ingredients and then allowing the mixture to stand for at least 24 hours; and after the recited mixture has been allowed to stand for at least 24 hours, adding about 10 ml. ginger oil to the mixture.

3. A method for making a homogeneous lecithin based topical liniment having a viscosity suitable for topical application comprising the steps of:

mixing together the following ingredients in parts per gallon and in the sequence listed:

about 560 g. of natural menthol;

about 10 g. of calcium stearate;

about 5 g. of magnesium stearate;

about 345 ml. of lemon grass oil;

about 230 ml. of clove oil;

about 190 ml. of eucalyptus oil;

about 125 ml. of lemon oil;

about 100 ml. of camphor oil;

about 40 ml. of lime oil;

said calcium stearate and said magnesium stearate providing a soluble stearate mixture which is miscible in said natural menthol and said recited oils and preventing precipitation thereof after mixing;

after mixing the above recited ingredients, adding about 8.5 cups of soybean lecithin to the mixture and mixing therewith and then allowing the mixture to stand for at least 24 hours; and then after allowing the mixture to stand for at least 24 hours, adding about 10 ml. of ginger oil to the recited mixture.

* * * * *